United States Patent
Fuimaono et al.

(10) Patent No.: US 6,905,495 B1
(45) Date of Patent: Jun. 14, 2005

(54) IRRIGATION PROBE FOR ABLATION DURING OPEN HEART SURGERY

(75) Inventors: Kristine B. Fuimaono, Covina, CA (US); Irma Hill, LaVerne, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 200 days.

(21) Appl. No.: 09/692,494

(22) Filed: Oct. 19, 2000

Related U.S. Application Data (63) Continuation-in-part of application No. 09/370,601, filed on Aug. 10, 1999.

(51) Int. Cl.[7] .............................................. A61B 18/18
(52) U.S. Cl. ......................... 606/41; 606/47; 607/122; 607/119; 600/374
(58) Field of Search .............................. 604/20, 21, 43, 604/44, 95.02, 95.05, 113, 114, 532, 500, 507–509; 606/41, 43, 45–50, 32; 607/113, 115, 119, 122; 600/152, 139, 144

(56) References Cited

U.S. PATENT DOCUMENTS

| | | | |
|---|---|---|---|
| 5,197,963 A | | 3/1993 | Parins ........................... 606/46 |
| 5,462,521 A | | 10/1995 | Brucker et al. ................ 604/20 |
| 5,555,883 A | * | 9/1996 | Avitall ........................... 600/374 |
| 5,643,197 A | | 7/1997 | Brucker et al. ................ 604/20 |
| 5,658,278 A | | 8/1997 | Imran et al. .................... 606/41 |
| 5,688,267 A | | 11/1997 | Panescu et al. ................ 606/41 |
| 5,730,127 A | * | 3/1998 | Avitall ........................... 600/374 |
| 5,735,846 A | | 4/1998 | Panescu et al. ................ 606/41 |
| 5,895,417 A | * | 4/1999 | Pomeranz et al. ............ 607/101 |
| 5,921,924 A | * | 7/1999 | Avitall ........................... 600/374 |
| 6,032,077 A | * | 2/2000 | Pomeranz ...................... 607/101 |
| 6,068,629 A | * | 5/2000 | Haissaguerre et al. ........ 606/41 |
| 6,071,279 A | * | 6/2000 | Whayne et al. ............... 606/41 |
| 6,076,012 A | * | 6/2000 | Swanson et al. .............. 604/21 |
| 6,325,797 B1 | * | 12/2001 | Stewart et al. ................ 606/41 |
| 6,332,881 B1 | * | 12/2001 | Carner et al. ................. 606/41 |
| 6,416,505 B1 | * | 7/2002 | Fleischman et al. .......... 606/1 |
| 6,428,537 B1 | * | 8/2002 | Swanson et al. .............. 606/41 |

OTHER PUBLICATIONS

Knaut et al., "Intraoperative Microwave Ablation for Curative Treatment of Atrial Fibrillation in Open Heart Surgery—The MICRO–STAF and MICRO–PASS Pilot Trial", *The Thoracic and Cardiovascular Surgeon*, vol. 47, Aug. 1999 (Supplement), pp. 379–384.

Hindrickes et al., "Antiarrhythmic Surgery for Treatment of Atrial Fibrillation—New Concepts", *The Thoracic and Cardiovascular Surgeon*, vol. 47, Aug. 1999 (Supplement), pp. 365–369.

* cited by examiner

*Primary Examiner*—Loan H. Thanh
*Assistant Examiner*—Cris L. Rodriguez
(74) *Attorney, Agent, or Firm*—Christie, Parker & Hale, LLP (57) ABSTRACT

An irrigation probe useful for ablation during open heart surgery is provided. The irrigation probe comprises a generally rigid probe body and a handle mounted to the proximal end of the probe body. The generally rigid probe body has an electrode at its distal end having at least one irrigation opening through which fluid can pass. An infusion tube extends through the probe body for introducing fluid to the electrode.

61 Claims, 7 Drawing Sheets

IRRIGATION PROBE FOR ABLATION DURING OPEN HEART SURGERY

CROSS-REFERENCE TO RELATED APPLICATION

This application is a continuation-in-part of U.S. application Ser. No. 09/370,601, filed Aug. 10, 1999, the disclosure of which is incorporated herein by reference.

FIELD OF THE INVENTION

The present invention is directed to an irrigation ablation probe for use during open heart surgery.

BACKGROUND OF THE INVENTION

Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy. It is believed that to treat atrial fibrillation by radio-frequency ablation using a catheter, continuous linear lesions must be formed to segment the heart tissue. By segmenting the heart tissue, no electrical activity can be transmitted from one segment to another. Preferably, the segments are made too small to be able to sustain the fibrillatory process.

It has been found that over 60% of patients with mitral valve problems also have atrial fibrillation. Moreover, patients undergoing open heart surgery commonly develop atrial fibrillation during the surgery, and thus it would be useful to address this problem during the surgery. Accordingly, under certain circumstances it may be desirable to treat atrial fibrillation during open heart surgery, for example, when a patient is undergoing a mitral valve replacement or repair procedure. Accordingly, a need exists for devices and methods for treating atrial fibrillation during open heart surgery.

SUMMARY OF THE INVENTION

The present invention is directed to an irrigation probe particularly useful for treating atrial fibrillation during open heart surgery. The probe of the present invention is also useful for other ablation and mapping procedures, particularly where irrigation of the ablation site is desired, such as for treating ventricular tachycardia. The invention is also directed to novel methods for treating atrial fibrillation with the probe of the invention. In accordance with the present invention, the probe comprises a rigid probe body and an irrigation electrode, which provides cooling and irrigation in the region of the tissue being ablated.

In one embodiment, the invention is directed to an irrigation ablation probe comprising a generally rigid probe body having proximal and distal ends. The probe body has an electrode at its distal end defining an inner cavity and having at least one irrigation opening through which fluid can pass and means for introducing fluid into the inner cavity. In a preferred embodiment an infusion tube having proximal and distal ends is in fluid communication with the inner cavity. In another preferred embodiment the infuision tube extends through the probe body for introducing fluid into the inner cavity of the electrode. In yet another preferred embodiment the electrode comprises an elongated body having first and second ends, which is fixedly attached, either directly or indirectly, to the distal end of the rigid probe body at a point along the elongated electrode body between its ends, wherein the angle formed between the distal end of the probe body and the electrode is greater than 0°. In still another preferred embodiment the electrode is attached generally perpendicular to the distal end of the rigid probe body and has at least three irrigation openings through which fluid can pass. In still yet another preferred embodiment the electrode comprises a flexible metal ribbon coiled around the outside of a looped irrigation tube fixedly attached, either directly or indirectly, to the distal end of the rigid probe body, where the irrigation tube has irrigation openings through which fluid can pass to the electrode and wherein the spaces between the coils provide openings through which fluid can pass to the outside of the irrigation probe.

In another embodiment, the invention is directed to an irrigation ablation probe. The probe comprises a generally rigid probe body as described above and a handle. The handle is mounted to the proximal end of the probe body. In a preferred embodiment, the generally rigid probe body comprises a tubular body, an elongated electrode having first and second ends mounted to the distal end of the rigid probe body at a point along the elongated electrode body between its ends, wherein the angle formed between the distal end of the probe body and the electrode is greater than 0°, and a non-conductive sheath covering the length of the probe body. In still yet another embodiment the electrode comprises a flexible metal ribbon coiled around the outside of a looped irrigation tube fixedly attached either directly or indirectly to the distal end of the rigid probe body, where the irrigation tube has irrigation openings through which fluid can pass to the electrode and wherein the space between the coils provide openings through which fluid can pass to the outside of the irrigation probe.

In another preferred embodiment, the generally rigid probe body comprises tubing having proximal and distal ends and at least one lumen extending therethrough. An electrode as described above is mounted at the distal end of the tubing. The electrode has at least one irrigation opening through which fluid can pass. The probe body further comprises means for introducing fluid through the irrigation opening(s) of the electrode and a stiffening wire extending through a lumen of the tubing. A preferred means for introducing fluid comprises an infusion tube that extends through a lumen of the tubing with the distal end of the infusion tube in fluid communication with the one irrigation opening(s) in the electrode. In one embodiment, an elongated electrode having first and second ends is mounted to the distal end of the rigid probe body at a point along the elongated electrode body between its ends, wherein the angle formed between the distal end of the probe body and the electrode is greater than 0°. In a preferred embodiment the electrode is fixedly attached, either directly or indirectly, generally perpendicular to the rigid probe body and has at least three irrigation openings through which fluid can pass. In another preferred embodiment, the electrode comprises a flexible metal ribbon coiled around the outside of a looped irrigation tube fixedly attached either directly or indirectly to the distal end of the rigid probe body, where the irrigation tube has irrigation openings through which fluid can pass to the electrode and wherein the space between the coils provide openings through which fluid can pass to the outside of the irrigation probe.

In still another embodiment, the invention is directed to a method for treating atrial fibrillation in a patient. The method comprises opening the heart of the patient and ablating at least one linear lesion in the heart tissue using an irrigation probe as described above.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION

Figure 1:
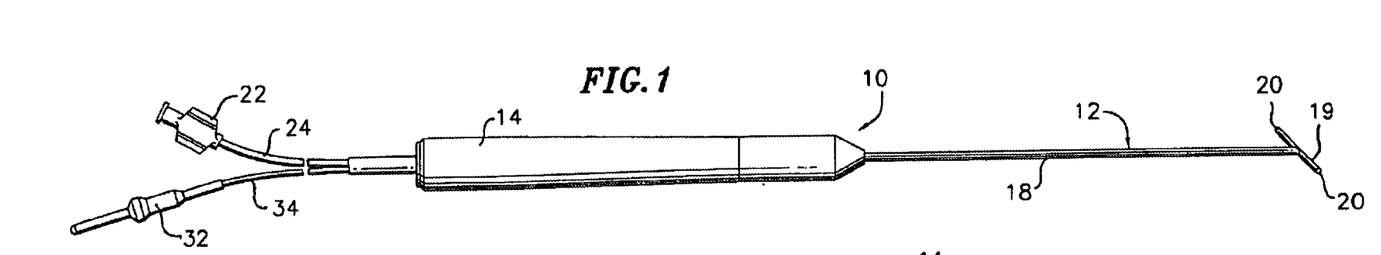
FIG. 1 is a side view of an embodiment of an irrigation probe according to the invention.
Figure 2:
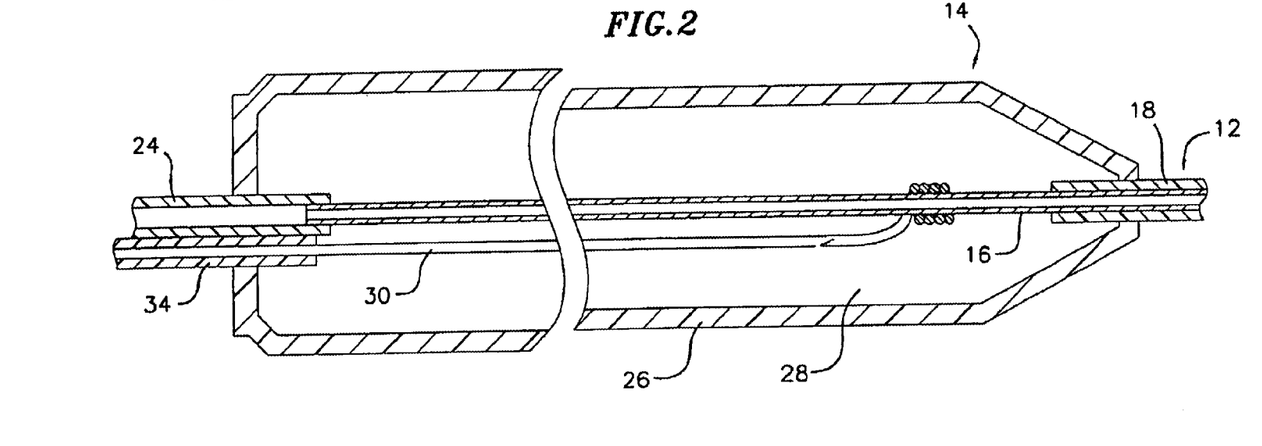
FIG. 2 is a side cross-sectional view of the handle of the irrigation probe of FIG. 1.

The present invention is directed to an irrigation probe for use during open heart surgery. In one embodiment, as shown in FIGS. 1 and 2, the irrigation probe 10 comprises a probe body 12 mounted to a handle 14. The probe body 12 comprises a tubular body 16, having proximal and distal ends, covered over by a non-conductive covering or sheath 18 along its length and an electrode 19 mounted at the distal end of the tubular body. The electrode 19 is a generally hollow tubular structure having two ends 20 and defining an inner cavity therein. The electrode 19 is generally perpendicular to the tubular body 16 and fixedly attached to the tubular body 16 at a point between the two ends 20 of the electrode. The junction of the tubular body 16 and the electrode 19 forms an angle α that is greater than 0°, preferably greater than 10°, more preferably greater than 20°, even more preferably ranging from 70 to 110°, still more preferably ranging from 85 to 95°. Still more preferably the electrode is fixedly attached at an angle α of about 90° relative to the distal end of the probe body, thus forming a generally T-shaped arrangement. The tubular body 16 extends the entire length of the probe body 12, with the proximal end of the tubular body extending into the handle 14 as described in more detail below. The probe body 12 preferably has a length (from the distal end of the handle to the distal end of the probe body) ranging from about 3.5 inches to about 12 inches, more preferably from about 5 to about 10 inches, still more preferably from about 7 to about 8 inches.

The tubular body 16 and the electrode 19 are both made of a material that is generally rigid so that the probe body 12 cannot bend during ablation, such as, for example, stainless steel (preferably 304VSS) or nitinol. Preferably the tubular body 16 and the electrode 19 have an inner diameter ranging from about 0.40 inch to about 0.80 inch, more preferably about 0.047 inch, and an outer diameter ranging from about 0.50 inch to about 0.90 inch, more preferably about 0.059 inch. If desired, the tubular body 16 and/or the electrode 19 can be heat-treated so that they are malleable enough to be bent by a physician to a desired shape but still rigid enough that they will not bend in use during a procedure. For example, for 304VSS stainless steel, the material is heated to about 800° F. with electrical current or in a salt bath. The hollow interior of the tubular body 16 forms a lumen through which saline and the like may be conducted to the inner cavity of the electrode 19 and from there infused during a procedure, as described in more detail below. Alternatively the tubular body 16 could be solid and fluids could be introduced into the inner cavity of the electrode 19 by a separate external tube or the like.

The non-conductive sheath 18 extends from a proximal end inside the handle 14 to a distal end at the union of the tubular body 16 and the electrode 19. The sheath 18 can be made of any suitable biocompatible non-conductive material, such as polyurethane. In this arrangement, the electrode 19 is exposed, i.e., not covered by the sheath 18, for ablating tissue, mapping, etc. Preferably the length of the electrode 19 ranges from about 0.50 inch to about 1.5 inches, more preferably from about 0.75 inch to about 1.25 inches.

In the depicted embodiment, the length of the probe body 12 is approximately 7 inches. The proximal section of the probe body 12, i.e., the portion extending from the handle 14, is approximately 5.5 inches. The length of the electrode 19, is approximately 1 inch.

Figure 3:
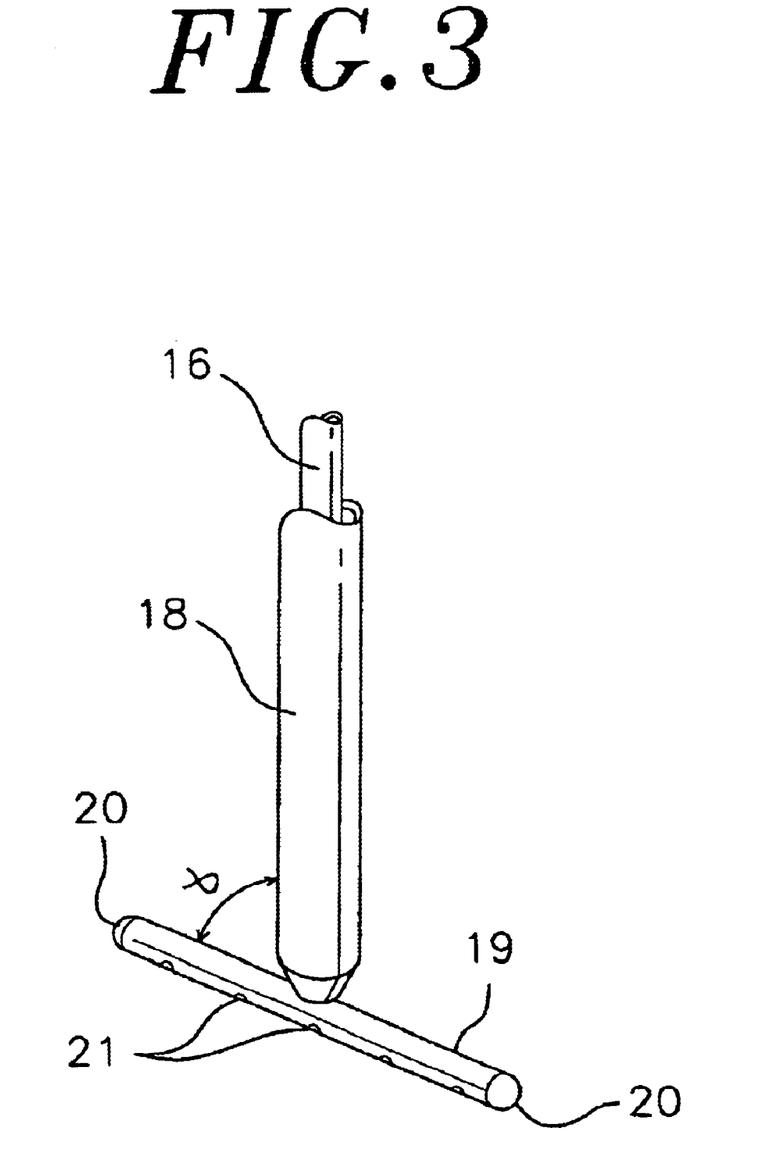
FIG. 3 is a perspective view of the distal end of the T-shaped irrigation probe of FIG. 1.

As shown in detail in FIG. 3, the electrode 19 has a series of irrigation openings 21 for passage of a cooling fluid out through the inner cavity of the electrode 19. The irrigation openings 21 can take any suitable shape, such as rectangular or oval slots or round holes. In a preferred embodiment the electrode 19 has at least three irrigation openings 21. The irrigation openings 21 are preferably in the section of the electrode 19 that is to be in contact with the tissue during a procedure, e.g., to enhance the cooling of an ablation site.

Saline or other suitable fluid is introduced into the inner cavity of the electrode 19 through any suitable means. In the embodiment of FIGS. 1 to 3, fluids are introduced into the inner cavity of the electrode 19 via the tubular body 16 through a luer hub 22 or the like at the proximal end of the probe 10. The luer hub 22 is connected to a flexible plastic tubing 24, e.g., made of polyimide. The plastic tubing 24 is attached, either directly or indirectly, to the proximal end of the tubular body 16, preferably within the handle 14, as shown in FIG. 2. Alternatively, the tubing 24 can be connected to a suction source (not shown) to permit aspiration of fluid from the region of tissue being operated on.

As shown in FIG. 2, the handle 14 comprises a housing 26 having a generally open interior 28. The tubular body 16 and sheath 18 extend into the distal end of the handle housing 26. In the depicted embodiment, the sheath 18 terminates a short distance proximal to the distal end of the housing 26. The tubular body 16 continues proximally beyond the sheath 18. The flexible plastic tubing 24 extends into the proximal end of the handle housing 26. The plastic tubing 24 is attached to the tubular body 16 within the open interior 28 of the handle, preferably at a point proximal to the proximal end of the sheath 18. The plastic tubing 24 can be attached to the tubular body 16 by any suitable means, for example, polyurethane glue. By this design, cooling fluid is introduced through the luer hub 22, though the plastic tubing 24, through the tubular body 16 and out the irrigation openings 21 in the electrode 19.

Alternatively, fluid could be supplied to the electrode 19 and thereby the irrigation openings 21 via a separate irrigation tube (not shown) that can either run external to the tubular body 16 and attach directly to the electrode 19, or can extend through the tubular body 16 to the electrode 19. In either, case this separate irrigation tube could be made of any suitable material, e.g., plastic or metal, and attach to the electrode 19 by any direct or indirect means.

An electrode lead wire 30 having proximal and distal ends is electrically connected at or adjacent its distal end to the probe body 16. The proximal end of the lead wire 30 is attached to a connector 32 for connection to a suitable source of ablation energy, e.g., radio frequency energy, or to an appropriate monitor. In the depicted embodiment, the lead wire 30 extends into the proximal end of the handle housing 26. Within the open interior 28 of the handle 14, the distal end of the lead wire 30 is wrapped around the portion of the tubular body 16 not covered by the sheath 18 and held in place by solder or the like. The portion of the lead wire 30 that extends outside the handle 14 is covered by a flexible plastic protective tubing 34, e.g., made of polyimide.

Figure 4:
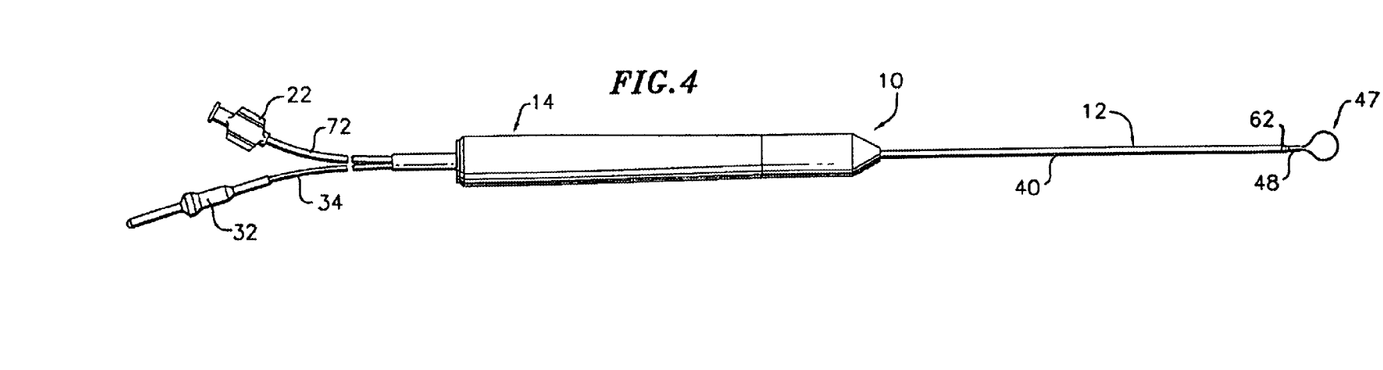
FIG. 4 is a side view of an alternative embodiment of an irrigation probe according to the invention.
Figure 5:
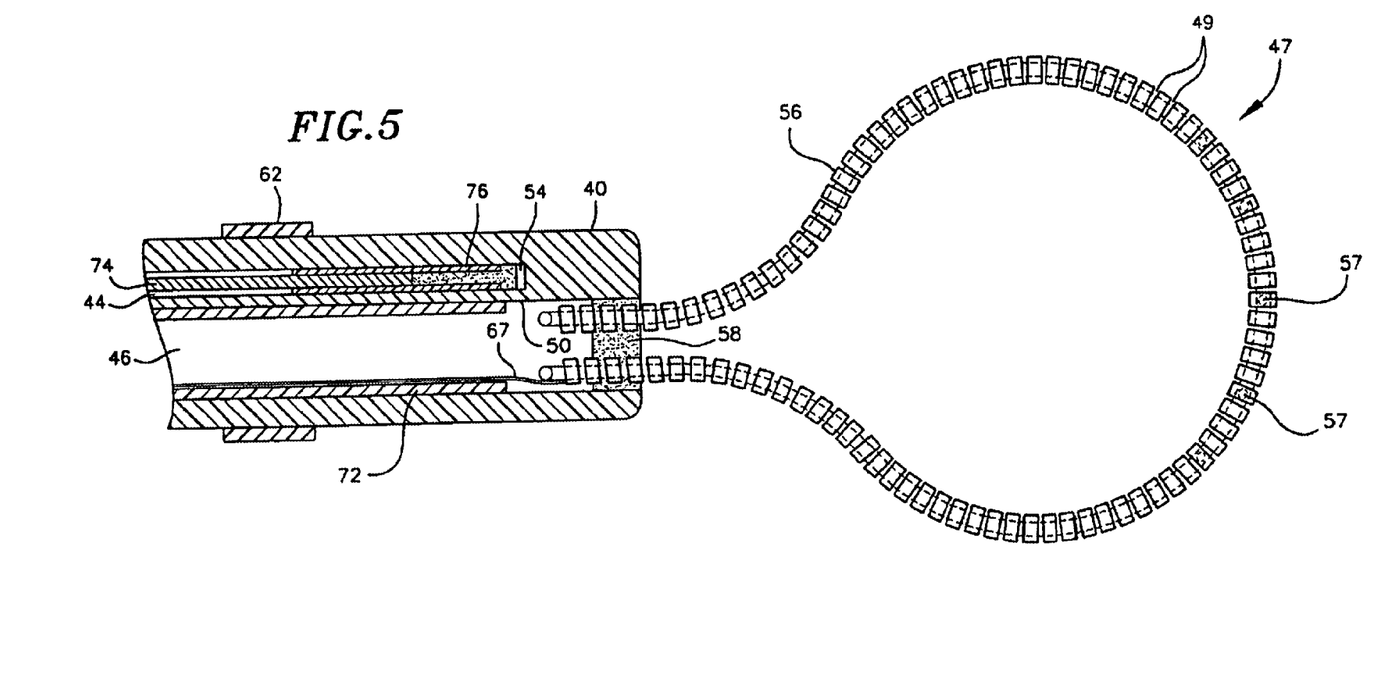
FIG. 5 is a side cross-sectional schematic view of the distal end of the flexible metal ribbon irrigation probe of FIG. 4, wherein the rigid probe body comprises at least one lumen.
Figure 6:
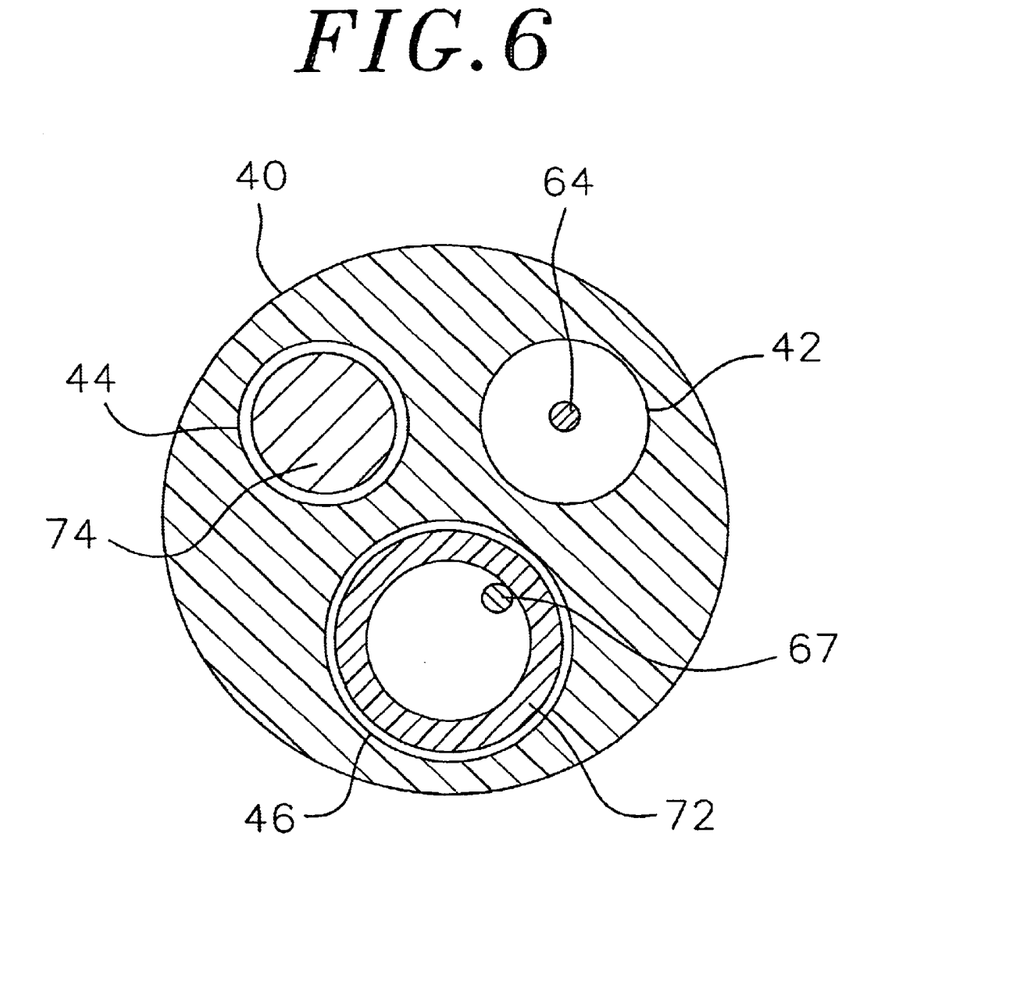
FIG. 6 is an end cross-sectional view of the distal end of the flexible metal ribbon irrigation probe of FIG. 4.

An alternative embodiment of an irrigation probe according to the invention is shown in FIGS. 4 to 6. As shown in FIG. 4, the probe 10 comprises a probe body 12 and a handle 14. The probe body 12 comprises a non-conductive tubing 40 having proximal and distal ends. In a particularly preferred embodiment, the non-conductive tubing 40 comprises outer and inner plastic walls, e.g., of polyurethane or polyimide, surrounding an imbedded braided mesh of stainless steel or the like. Preferably the tubing has an outer diameter of less than 8 French, more preferably less than 7 French. The tubing 40 has three lumens 42, 44 and 46 extending along its length.

The irrigation probe comprises a metal ribbon electrode 47 at the distal end 48 of the non-conducting tube 40 comprising an exposed metallic ribbon 49 that is coiled around a loop of irrigation tubing 56, both of which are indirectly or directly fixedly attached to the distal end 48 of the non-conducting tube 40. As illustrated in FIG. 5, the probe's distal end 48 is generally solid, having a fluid passage 50, a first blind hole (not shown) and a second blind hole 54 corresponding in size and location to the three lumens 46, 42 (FIG. 6), and 44, respectively, in the non-conductive tubing 40. In the embodiment shown, the fluid passage 50 is in fluid communication with the inner cavity of the flexible irrigation tube 56, which extends from the distal end of the fluid carrying lumen 46 out of the probe's distal end 48. The irrigation tube 56 has a series of irrigation openings 57 for passage of a cooling fluid out through the spaces between the coils of the metallic ribbon 49, as described in more detail below. The irrigation openings 57 can take any suitable shape, such as rectangular or oval slots or round holes. In a preferred embodiment the irrigation tubing 56 has at least three irrigation openings 57. The irrigation openings 57 are preferably in the section of the irrigation tubing 56 corresponding to the section of the metal ribbon electrode 47 that is to be in contact with the tissue during an ablation procedure to enhance the cooling of the ablation site.

The metallic ribbon 49 is coiled loosely around the irrigation tube 56 such that fluid can pass unimpeded to the outside of the metal ribbon electrode 47. The metal ribbon electrode 47, as shown in detail in FIG. 5, comprises a continuous ribbon 49 of conducting metal, extending outside of the probe's distal end 48 and coiled about the flexible irrigation tube 56 in a loop, having a radius ranging from about 0.5 inch to 1.5 inches. The metal ribbon 49 can be coiled in any manner wherein the coils of the metal ribbon define an inner tubular passage through which the irrigation tube 56 runs and wherein the coils of metal ribbon 49 are generally spaced sufficiently far apart to allow fluid to escape through the irrigation passages. In a preferred embodiment the metal ribbon electrode 49 is coiled around from 1% to 100% of the length of the irrigation tube 56 that is outside the probe body 12. More preferably, the metal ribbon 49 is coiled around from 20% to 80% of the length of the irrigation tube 56, still more preferably the metal ribbon electrode is coiled around from 40% to 60% of the length of the irrigation tube 56. The metal ribbon 49 can be made of any suitable material, and is preferably machined from a 0.005 inch thick ribbon of nitinol.

The metal ribbon 49 and the irrigation tube 56 can be attached to the probe's distal end 48 in any suitable manner. In the depicted embodiment, the metal ribbon 49 and the irrigation tube 56 are each attached at both ends to the probe's distal end 48 by a polyurethane glue seal 58 or the like. However, any other means for fixedly mounting the metal ribbon 49 and the irrigation tube 56 on the probe's distal end 48 can also be used. For example, only one end of the metal ribbon 49 and/or the irrigation tube 56 may be attached to the probe's distal end 48.

The metal ribbon electrode 47 is connected to a lead wire 67 having proximal and distal ends. The proximal end of the lead wire 67 for the metal ribbon electrode 47 extends through the third lumen 46 of tubing 40 and through the handle 14. The distal end of the lead wire 67 for the metal ribbon electrode 47 extends through the third lumen 46 and is attached to the metal ribbon electrode 47 by any conventional technique, for example, by soldering.

In the embodiment shown, a mapping ring electrode 62 is mounted on the tubing 40 proximal to the probe's distal end 48. It is understood that the presence and number of ring electrodes may vary as desired. The ring electrode 62 is slid over the tubing 40 and fixed in place by glue or the like. The ring electrode 62 can be made of any suitable material, and is preferably machined from platinum-iridium bar (90% platinum/10% iridium).

The ring electrode 62 is connected to a lead wire 64 having proximal and distal ends. The proximal end of the lead wire 64 for the ring electrode 62 extends through the first lumen 42 of tubing 40 and through the handle 14. The lead wire 64 can be connected to the ring electrode 62 by any conventional technique. Connection of the lead wire 64 to the ring electrode 62 is preferably accomplished by first making a small hole through the tubing 40. Such a hole can be created, for example, by inserting a needle through the tubing 40 and heating the needle sufficiently to form a permanent hole. The lead wire 64 is then drawn through the hole by using a microhook or the like. The ends of the ring electrode lead wire 64 are then stripped of any coating and soldered or welded to the underside of the ring electrode 62, which is then slid into position over the hole and fixed in place with polyurethane glue or the like. Any other means for fixedly mounting the ring electrode 62 to the tubing 40 can also be used Both lead wires 64 and 67 terminate at their proximal end in a connector 32 that may be plugged into an appropriate monitor and/or source of radio frequency or other ablation energy. The portion of the lead wires 64 and 67 extending out the proximal end of the handle 14 are enclosed within a protective tubing 34, which can be made of any suitable material, preferably polyimide, as shown in FIG. 4.

An infusion tube 72 is provided for infusing fluids, e.g., saline, to cool the metal ribbon electrode 47 during ablation. The infusion tube 72 may also be used to infuse drugs to the ablation site. The infusion tube 72 may be made of any suitable material, and is preferably made of polyimide tubing. The infusion tube 72 has proximal and distal ends, with its distal end mounted in the fluid passage 50 of the probe's distal end 48 by any suitable method, e.g., by polyurethane glue or the like. The infusion tube 72 extends from the probe's distal end 48, through the third lumen 46 of the tubing 40, and through the handle 14. As would be recognized by one skilled in the art, the distal end of the infusion tube 72 can be positioned at any point within the third lumen 46. The proximal end of the infusion tube 72 ends in a luer hub 22 or the like. Any other means for infusing fluids to the metal ribbon electrode 47 can also be used, including running the infusion tube 72 external to the tubing 40 and fluid passage 50.

A stiffening wire 74, having proximal and distal ends, is mounted in the second lumen 44 of the tubing 40. The stiffening wire 74 is made of a rigid metal or plastic material, preferably stainless steel, to prevent the probe body 12 from bending during a procedure. If desired, the stiffening wire 74 can be heat-treated so that it is malleable and can be bent to a desired shape before use, but still rigid enough that it will not bend in use during a procedure. A non-conductive tube 76, preferably made of polyimide, is attached to the distal end of the stiffening wire 74 for mounting the stiffening wire in the probe's distal end 48. The non-conductive tube 76 extends out of the second lumen 44 and into the second blind hole 54 in the probe's distal end 48, and is secured in place by polyurethane glue or the like. Any other means for securing the stiffening wire 74 within the probe can also be used. The proximal end of the stiffening wire 74 terminates in the handle 14 or near the proximal end of the probe body 12.

While FIGS. 4 to 6 depict an irrigation probe 10 having a metal ribbon electrode 47, it will be understood that the irrigation probe 10 described above and illustrated in FIGS. 4 to 6 could also house the generally T-shaped electrode 19 illustrated in FIGS. 1 to 3. In this embodiment the generally T-shaped electrode 19 is fixedly attached, either directly or indirectly, to the probe's distal end 48 such that the fluid passage 50 is in fluid communication with the inner cavity of the generally T-shaped electrode 19. The construction and function of the lumens 42, 44, and 46, and the remainder of the probe 10 would be similar to that described above and shown in FIGS. 4 to 6.

Figure 7:
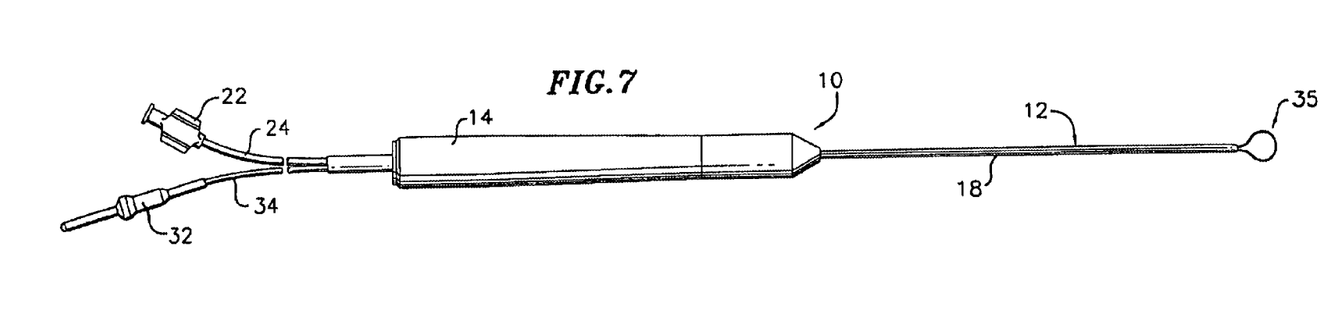
FIG. 7 is a side view of an alternative embodiment of an irrigation probe according to the invention.
Figure 8:
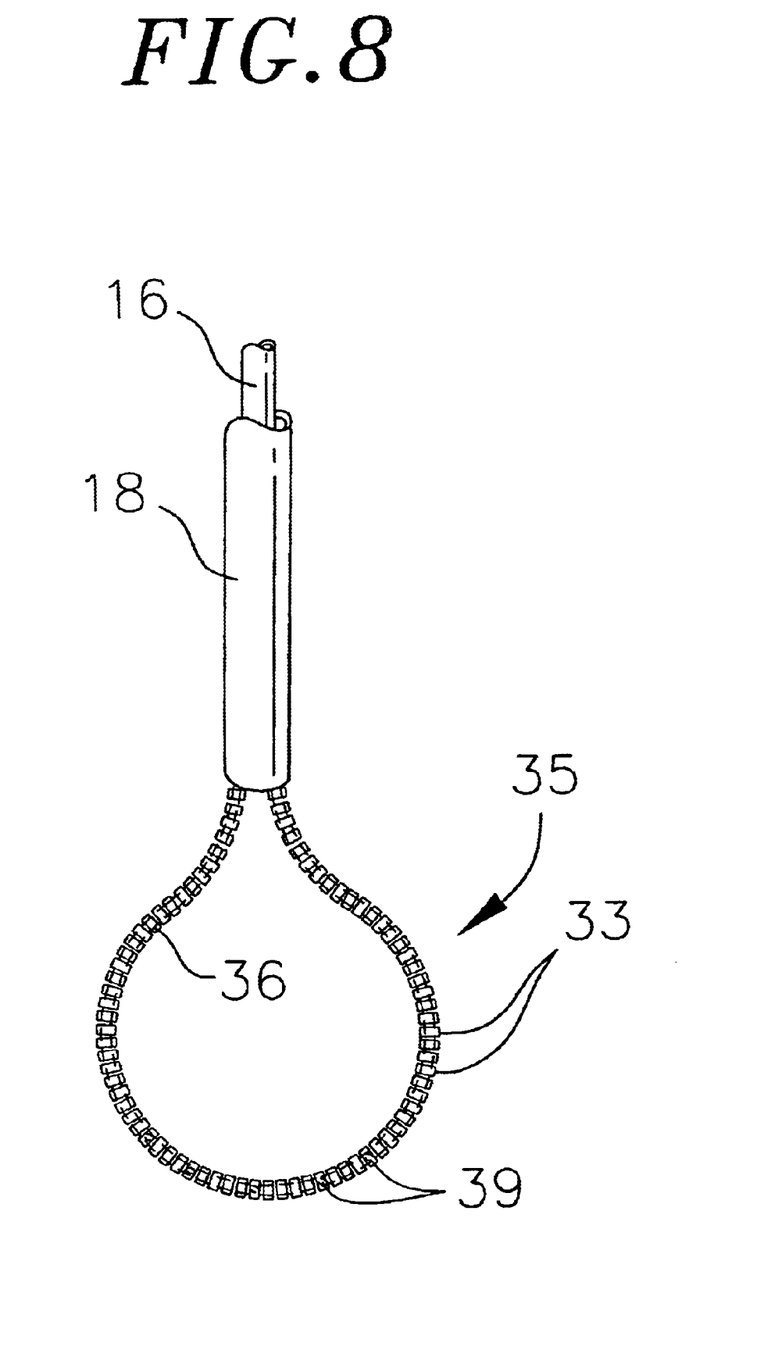
FIG. 8 is a perspective view of the distal end of the flexible metal ribbon irrigation probe of FIG. 7.

In another embodiment, as shown in FIGS. 7 and 8, the irrigation probe 10 comprises a probe body 12 mounted to a handle 14, which is described in detail above. The probe body 12 comprises a tubular body 16, having proximal and distal ends, covered over by a non-conductive covering or sheath 18. In this embodiment, a metal ribbon electrode 35 comprising a coiled metal ribbon 33 and a loop of flexible irrigation tube 36 is disposed at the distal end of the probe body 12 and fixedly attached, either directly or indirectly, to the distal end of the tubular body 16. The probe body 12 preferably has a length (from the distal end of the handle to the distal end of the probe body) ranging from about 3.5 inches to about 12 inches, more preferably from about 5 to about 10 inches, still more preferably from about 7 to about 8 inches.

The tubular body 16 is made of a material that is generally rigid so that the probe body 12 cannot bend during ablation, such as, for example, stainless steel (preferably 304VSS) or nitinol. Preferably the tubular body 16 has an inner diameter ranging from about 0.40 inch to about 0.80 inch, more preferably about 0.047 inch, and an outer diameter ranging from about 0.50 inch to about 0.90 inch, more preferably about 0.059 inch. If desired, the tubular body 16 can be heat-treated so that it is malleable enough to be bent by a physician to a desired shape but still rigid enough that it will not bend in use during an ablation procedure. The hollow interior of the tubular body 16 forms a lumen through which saline and the like may be conducted to the irrigation tube 36 of the metal ribbon electrode 35 and from there infused during an ablation procedure, as described in more detail below. Alternatively, the tubular body 16 could be solid, in which case fluids could be introduced into the irrigation tube 36 via a separate external tube or the like.

The non-conductive sheath 18 extends from the proximal end of the tubular body 16 inside the handle 14 to the distal end of the tubular body at the union of the tubular body 16 and the metal ribbon electrode 35. The sheath 18 can be made of any suitable biocompatible non-conductive material, such as polyurethane. Preferably the diameter of the loop of the metal ribbon electrode 35 ranges from about 0.50 inch to about 1.5 inches, more preferably from about 0.75 inch to about 1.25 inches.

In the depicted embodiment, the length of the probe body 12 is approximately 7 inches. The proximal section of the probe body 12, i.e., the portion extending from the handle 14, is approximately 5.5 inches. The diameter of the loop of the metal ribbon electrode 35 is approximately 1 inch.

As shown in detail in FIG. 8, the metal ribbon electrode 35 comprises an irrigation tube 36 having first and second ends 37, at least one of which is fixedly attached either directly or indirectly to the tubular body 16, similar to the embodiment depicted in FIGS. 4 to 6. The irrigation tube 36 is bent so as to form a loop and the metal ribbon 33 is in turn coiled around the irrigation tube 36 and fixedly attached, either directly or indirectly, to the tubular body 16. In one preferred embodiment, the metal ribbon 33 and irrigation tube 36 are both attached to the tubular body 16 at both ends by any direct or indirect means, e.g., via a glue seal 38 as shown above in FIG. 5. Any other means for attaching the metal ribbon 33 and the irrigation tube 36 can also be used.

As shown, the irrigation tube 36 has a series of irrigation openings 39 for passage of a cooling fluid out through the metal ribbon 33. The irrigation openings 39 can take any suitable shape, such as rectangular or oval slots or round holes. In a preferred embodiment, shown in FIG. 8, the irrigation tube 36 has at least three irrigation openings 39. The irrigation openings 39 are preferably in the section of the irrigation tube 36 corresponding to the section of the metal ribbon 33 that is to be in contact with the tissue during a procedure, e.g., to enhance the cooling of the ablation site. The metal ribbon 33 is coiled loosely around the irrigation tube 36 such that fluid can pass unimpeded through the metal ribbon 33.

Saline or other suitable fluid is introduced into the tubular body 16 through a luer hub 22 or the like at the proximal end of the probe 10. The luer hub 22 is connected to a flexible plastic tubing 24, e.g., made of polyimide. The plastic tubing 24 is attached, either directly or indirectly, to the proximal end of the tubular body 16, preferably within the handle 14, as shown in FIG. 7. By this design, cooling fluid is introduced through the luer hub 22, though the plastic tubing 24, through the tubular body 16, through the first and second ends 37 of the irrigation tube 36 and out the irrigation openings 39.

The irrigation probe shown in various embodiments in FIGS. 1 to 8, having either a metal ribbon electrode or a generally T-shaped electrode, can be used in any manner in which a standard probe can be used. For example, the above described probes can be used during open heart surgery for ablation. During an ablation procedure, the heart is opened and the irrigated electrode is used to form continuous linear lesions by ablation As used herein, a linear lesion refers to any lesion, whether curved or straight, between two anatomical structures in the heart that is sufficient to block a wavelet, i.e., forms a boundary for the wavelet. Anatomical structures, referred to as "atrial trigger spots", are those regions in the heart having limited or no electrical conductivity and are described in Haissaguerre et al., "Spontaneous Initiation of Atrial Fibrillation by Ectopic Beats Originating in the Pulmonary Veins", New England Journal of Medicine, 339:659–666 (Sep. 3, 1998), the disclosure of which is incorporated herein by reference. The linear lesions typically have a length of from about 1 cm to about 4 cm, but can be longer or shorter as necessary for a particular procedure.

The probe described in FIGS. 1 to 3 having a long tubular electrode is particularly useful for this procedure because it can create relatively long lesions. The probe depicted in FIGS. 4 to 6 above, having a smaller but flexible ablation electrode, is useful if the surgeon does not want to ablate as much tissue or wants to ablate a more precise lesion. The above-described probe having a flexible body is particularly useful if the surgeon needs to have a probe that conforms to a particular site to better ablate a desired region of tissue. Additionally, the flexible electrode is particularly useful for ablating locations where it is desirable to have the electrode conform to the tissue, rather than having the tissue conform to the electrode, for example, an atrial appendage. Further, the circular coil design can be used to form a generally circular region around an orifice of a tubular structure, such as a pulmonary vein, the coronary sinus, the superior vena cava, or the inferior vena cava. Once the heart is closed, the surgeon can use the probe on the outside of the heart, not only to ablate, but to verify that the electrical conduction has been stopped using the mapping electrodes. As would be recognized by one skilled in the art, the probes of the present invention can be used during open heart surgery for other procedures as well.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. An irrigation probe comprising:
    a generally rigid probe body having proximal and distal ends;
    a generally flexible irrigation tube having first and second ends, the irrigation tube defining an inner cavity, wherein the irrigation tube generally forms a loop, wherein the first end of the irrigation tube is fixedly attached at a first location on the distal end of the probe body and the second end of the irrigation tube is fixedly attached at a second location on the distal end of the probe body, the irrigation tube having at least one irrigation opening through which fluid can pass from the inner cavity to the outside of the irrigation tube;
    means for introducing fluid into the inner cavity of the irrigation tube; and
    a continuous electrode comprising a flexible metal ribbon having first and second ends, wherein the metal ribbon is coiled around the irrigation tube to form coils, and wherein space is provided between the coils to allow fluid to pass from the irrigation tube to the outside of the electrode.

2. An irrigation probe according to claim 1, wherein the probe body has a length ranging from about 3.5 inches to about 12 inches.

3. An irrigation probe according to claim 1, wherein the probe body has a length ranging from about 5 inches to about 10 inches.

4. An irrigation probe according to claim 1, wherein the first end of the metal ribbon electrode is fixedly attached at a first location on the distal end of the probe body, and the second end of the metal ribbon electrode is fixedly attached at a second location on the distal end of the probe body.

5. An irrigation probe according to claim 1, wherein the probe further comprises an electrode lead wire with proximal and distal ends, wherein the proximal end of the electrode lead wire is electrically connected to a source of ablation energy and the distal end of the electrode lead wire is electrically connected to the electrode.

6. An irrigation probe according to claim 1, wherein the means for introducing fluid into the inner cavity comprises an infusion tube having proximal and distal ends, wherein the distal end of the infusion tube is in fluid communication with the inner cavity.

7. An irrigation probe according to claim 6, further comprising a handle mounted at the distal end of the probe body, the handle comprising a housing having a generally open interior.

8. An irrigation probe according to claim 1, wherein the generally rigid probe body comprises a malleable material.

9. An irrigation probe according to claim 1, wherein the flexible metal ribbon is made of nitinol.

10. An irrigation probe according to claim 1, wherein the metal ribbon electrode is coiled around about 100% of the length of the loop formed by the irrigation tube.

11. An irrigation probe according to claim 1, wherein the metal ribbon electrode is coiled around from about 80% of the length of the loop formed by the irrigation tube.

12. An irrigation probe according to claim 1, wherein the metal ribbon electrode is coiled around about 60% of the length of the loop formed by the irrigation tube.

13. An irrigation probe according to claim 1, wherein the metal ribbon electrode is coiled around about 40% of the length of the loop formed by the irrigation tube.

14. A method for treating atrial fibrillation in a patient comprising:
    opening the heart of the patient; and
    ablating at least one linear lesion in the heart tissue using an irrigation probe as recited in claim 1.

15. An irrigation probe comprising:
    a generally rigid probe body having proximal and distal ends;
    a generally flexible irrigation tube having first and second ends, the irrigation tube defining an inner cavity, wherein the irrigation tube generally forms a loop and both the first and second ends are separately fixedly attached to the distal end of the probe body, the irrigation tube having at least one irrigation opening through which fluid can pass from the inner cavity to the outside of the irrigation tube;
    a continuous electrode comprising a flexible metal ribbon having first and second ends, wherein the metal ribbon is coiled around from about 20% to about 100% of the length of the loop formed by the irrigation tube, the metal ribbon forming coils, and wherein space is provided between the coils to allow fluid to pass from the irrigation tube to the outside of the electrode;

a handle mounted to the proximal end of the probe body; and an infusion tube having proximal and distal ends, wherein the distal end of the infusion tube is in fluid communication with the inner cavity.

16. An irrigation probe according to claim 15, wherein the generally rigid probe body comprises:

a generally rigid tubular body having proximal and distal ends, wherein the tubular body has at least one irrigation opening at its distal end through which fluid can pass to the inner cavity of the irrigation tube; and a non-conductive sheath covering the tubular body.

17. An irrigation probe according to claim 16, wherein the tubular body has an outer diameter ranging from about 0.50 inch to about 0.70 inch.

18. An irrigation probe according to claim 16, wherein the tubular body has an inner diameter ranging from about 0.40 inch to about 0.60 inch.

19. An irrigation probe according to claim 16, wherein the tubular body has an inner diameter ranging from about 0.40 inch to about 0.80 inch and an outer diameter ranging from about 0.5 inch to about 0.90 inch.

20. An irrigation probe according to claim 16, wherein the tubular body is made of a malleable material.

21. An irrigation probe according to claim 16, further comprising a flexible plastic tubing attached to the proximal end of the tubular body for introducing fluid into the tubular body.

22. An irrigation probe according to claim 15, wherein the probe body has a length ranging from about 3.5 inches to about 12 inches.

23. An irrigation probe according to claim 15, wherein the probe body has a length ranging from about 7 inches to about 8 inches.

24. An irrigation probe according to claim 15, wherein the loop has a diameter ranging from about 0.50 inch to about 1.5 inches.

25. An irrigation probe according to claim 15, wherein the loop has a diameter ranging from 0.75 inch to about 1.25 inches.

26. An irrigation probe according to claim 15, wherein the metal ribbon is made of nitinol.

27. An irrigation probe according to claim 15, wherein the generally rigid probe body comprises:

tubing having proximal and distal ends and first and second lumens extending therethrough, wherein the irrigation tube and electrode are mounted at the distal end of the tubing;

an infusion tube that extends at least part of the way through the first lumen of the tubing, wherein the distal end of the infusion tube is in fluid communication with the inner cavity of the irrigation tube; and a stiffening wire having proximal and distal ends that extends through the second lumen of the tubing.

28. An irrigation probe according to claim 27, wherein the stiffening wire is made of a malleable material.

29. An irrigation probe according to claim 27, wherein the probe body has a length ranging from about 3.5 inches to about 12 inches.

30. An irrigation probe according to claim 27, wherein the probe body has a length ranging from about 7 inches to about 8 inches.

31. An irrigation probe according to claim 15, wherein the metal ribbon electrode is coiled around about 100% of the length of the loop formed by the irrigation tube.

32. An irrigation probe according to claim 15, wherein the metal ribbon electrode is coiled around about 80% of the length of the loop formed by the irrigation tube.

33. An irrigation probe according to claim 15, wherein the metal ribbon electrode is coiled around about 60% of the length of the loop formed by the irrigation tube.

34. An irrigation probe according to claim 15, wherein the metal ribbon electrode is coiled around about 40% of the length of the loop formed by the irrigation tube.

35. An irrigation probe according to claim 15, wherein the metal ribbon electrode is coiled around about 20% of the length of the loop formed by the irrigation tube.

36. A method for treating atrial fibrillation in a patient comprising:

opening the heart of the patient, and ablating at least one linear lesion in the heart tissue using an irrigation probe as recited in claim 15.

37. A method according to claim 36, wherein the generally rigid probe body comprises:

tubing hiving proximal and distal ends and first and second lumens extending therethrough, wherein the electrode is mounted at the distal end of the tubing;

a stiffening wire having proximal and distal ends that extends through the second lumen of the tubing; and an infusion tube that extends at least a part of the way through the first lumen of the tubing, wherein the distal end of the infusion tube is in fluid communication with the inner cavity of the irrigation tube.

38. A method according to claim 37, wherein the stiffening wire is made of a malleable material.

39. A method according to claim 36, wherein the probe body has a length ranging from about 3.5 inches to about 12 inches.

40. A method according to claim 36, wherein the probe body has a length ranging from about 5 inches to about 10 inches.

41. A method according to claim 36, wherein the probe body has a length ranging from about 7 inches to about 8 inches.

42. A method according to claim 36, wherein the generally rigid probe body comprises:

a generally rigid tubular body having proximal and distal ends, wherein the tubular body has at least one irrigation opening at its distal end through which fluid can pass to the inner cavity of the irrigation tube; and a non-conductive sheath covering the tubular body.

43. A method according to claim 42, wherein the tubular body has an inner diameter ranging from about 0.40 inch to about 0.80 inch and an outer diameter ranging from about 0.50 inch to about 0.90 inch.

44. A method according to claim 42, wherein the tubular body is made of a malleable material.

45. A method according to claim 42, further comprising a flexible plastic tubing attached to the proximal end of the tubular body f or introducing fluid into the tubular body.

46. A method according to claim 36, wherein the loop has a diameter ranging from about 0.50 inches to about 1.5 inches.

47. A method according to claim 36, wherein the loop has a diameter ranging from about 0.75 inch to about 1.25 inches.

48. A method according to claim 36, wherein the metal ribbon is made of nitinol.

49. An irrigation probe comprising:

a generally rigid probe body having proximal and distal ends;

a generally flexible irrigation tube having first and second ends, the irrigation tube defining an inner cavity through which no other components extend, wherein the irrigation tube generally forms a loop and at least one end is fixedly attached to the distal end of the probe body, the irrigation tube having at least one irrigation opening through which fluid can pass from the inner cavity to the outside of the irrigation tube;

means for introducing fluid into the inner cavity of the irrigation tube; and a continuous electrode comprising a flexible metal ribbon having first and second ends, wherein the metal ribbon is coiled repeatedly around from about 20% to about 100% of the length of the loop formed by the irrigation tube, the metal ribbon forming coils, and wherein space is provided between the coils to allow fluid to pass from the irrigation tube to the outside of the electrode, and wherein the first and second ends of the metal ribbon extend into the distal end of the probe body.

50. An irrigation probe according to claim 49, wherein both the first and second ends of the irrigation tube are fixedly attached to the distal end of the probe body.

51. An irrigation probe according to claim 50, wherein the first end of the irrigation tube is fixedly attached at a first location on the distal end of the probe body, and the second end of the irrigation tube is fixedly attached at a second location on the distal end of the probe body.

52. An irrigation probe according to claim 49, wherein the probe further comprises an electrode lead wire with proximal and distal ends wherein the proximal end of the electrode lead wire is electrically connected to a source of ablation energy and the distal end of the electrode lead wire is electrically connected to the electrode.

53. An irrigation probe according to claim 49, wherein the means for introducing fluid into the inner cavity comprises an infusion tube having proximal and distal ends, wherein the distal end of the infusion tube is in fluid communication with the inner cavity.

54. An irrigation probe according to claim 49, wherein the generally rigid probe body comprises a malleable material.

55. An irrigation probe according to claim 49, wherein the flexible metal ribbon is made of nitinol.

56. An irrigation probe according to claim 49, wherein the metal ribbon electrode is coiled around about 80% of the length of the loop formed by the irrigation tube.

57. An irrigation probe according to claim 49, wherein the metal ribbon electrode is coiled around about 60% of the length of the loop formed by the irrigation tube.

58. An irrigation probe according to claim 49, wherein the metal ribbon electrode is coiled around about 40% of the length of the loop formed by the irrigation tube.

59. A method for treating atrial fibrillation in a patient comprising:

opening the heart of the patient; and ablating at least one linear lesion in the heart tissue using an irrigation probe as recited in claim 49.

60. A method according to claim 59, wherein the loop has a diameter ranging from about 0.50 inch to about 1.5 inches.

61. A method according to claim 59, wherein the loop has a diameter ranging from about 0.75 inch to about 1.25 inches.

* * * * *

UNITED STATES PATENT AND TRADEMARK OFFICE
CERTIFICATE OF CORRECTION

PATENT NO. : 6,905,495 B1  Page 1 of 1
DATED : June 14, 2005
INVENTOR(S) : Fuimaono et al.

It is certified that error appears in the above-identified patent and that said Letters Patent is hereby corrected as shown below:

<u>Title page,</u>
Item [56], References Cited, OTHER PUBLICATIONS,
"Hindricks et al.," reference, delete "Hindrickes", insert -- Hindricks --.

<u>Column 11,</u>
Line 56, delete "extends", insert -- extend --.

<u>Column 12,</u>
Line 15, delete ",", insert -- ; --.
Line 55, delete "f or", insert -- for --.

Signed and Sealed this

Second Day of May, 2006

JON W. DUDAS
*Director of the United States Patent and Trademark Office*